United States Patent [19]
Dale et al.

[11] Patent Number: 6,032,474
[45] Date of Patent: Mar. 7, 2000

[54] EVIDENCE PRESERVATION SYSTEM

[75] Inventors: William M. Dale; Joseph C. Burch, both of Ballston Lake; Harold M. Hatfield, Clifton Park; Robert J. McGee, Rensselaer, all of N.Y.

[73] Assignee: Forensic Solutions, Inc., Waterford, N.Y.

[21] Appl. No.: 09/087,046

[22] Filed: May 29, 1998

[51] Int. Cl.$^7$ ..................................................... B60H 1/32
[52] U.S. Cl. ........................................... 62/239; 62/457.9
[58] Field of Search ................................. 62/239, 457.1, 62/457.9; 454/158, 236

[56] References Cited

U.S. PATENT DOCUMENTS

| | | | |
|---|---|---|---|
| 2,034,472 | 3/1936 | Kesslinger | 62/457.1 |
| 3,089,313 | 5/1963 | Fix | 62/239 |
| 4,633,767 | 1/1987 | Sain | 62/239 |
| 4,979,431 | 12/1990 | Fujimoto et al. | 62/239 |
| 5,129,235 | 7/1992 | Renken et al. | 62/239 |
| 5,584,188 | 12/1996 | Tippmann et al. | 62/239 |

*Primary Examiner*—William E. Tapolcai
*Attorney, Agent, or Firm*—Heslin & Rothenberg, P.C.

[57] ABSTRACT

A portable evidence preservation system for storing and transporting forensic evidence, in particular items containing blood, fibers, hair, and semen samples, in one or more generally energy-efficient, cool, dry, contaminate-free, isolated chambers. The system includes a housing having a plurality of chambers for storing and transporting forensic evidence therein, an HVAC unit for providing, and desirably recirculating, a supply of air through the chambers and for maintaining the supply of air at a predetermined temperature and at a predetermined humidity. A plurality of HEPA-type filters separately filters the supply of air to each chamber. The cool, dry air in the chambers inhibits and reduces the rate of the growth of bacteria which can destroy DNA and other proteins in the items of evidence containing blood and semen samples. The HEPA-type filters are effective to reduce cross-contamination between items in a chamber and between items in different chambers. The HEPA-type filters are also effective to trap airborne bacteria in the supply of air.

45 Claims, 7 Drawing Sheets

EVIDENCE PRESERVATION SYSTEM

The present invention relates generally to systems for preserving forensic evidence. More particularly, the present invention relates to novel portable evidence preservation systems for storing over long term and/or transporting forensic evidence in one or more generally energy-efficient, cool, dry, contaminate-free, isolated chambers, from a first location to a second location.

BACKGROUND OF THE INVENTION

Evidence gathered during a criminal investigation must be properly collected, recorded, analyzed, and stored from the time it is discovered until it is presented in court. Often the most crucial items of evidence gathered during a criminal investigation are items of evidence containing blood, fibers, hair, and semen samples.

One problem with preserving such items of evidence is deterioration. In particular, bacteria can destroy DNA and other proteins in such items of evidence. In addition, moisture and increased temperatures accelerate bacterial growth.

Another problem with preserving such items of evidence is contamination which can occur between various items in one criminal case between items in separate criminal cases, and when transporting the items of evidence among crime scenes, hospitals, police departments, forensic laboratories, and/or court buildings.

In addition, personnel who collect and store such items of evidence are at risk to blood-borne pathogens in or on such items of evidence, and to airborne pathogens and noxious odors emitted from such items of evidence.

Furthermore, the storage of evidence also requires a sturdy, tamper proof construction that safeguards the evidence from theft or loss.

Therefore, there is need for novel portable evidence preservation systems for storing and transporting items of evidence, e.g., blood, fibers, hair, and semen samples, which reduce the likelihood and/or rate of deterioration of such items of evidence, which reduce contamination of such items of evidence, which reduce biological risks to personnel from such items of evidence, and which ensures the integrity and security of the evidence from theft, tampering, and/or loss.

SUMMARY OF THE INVENTION

The problems associated with storing and transporting forensic evidence are overcome, and additional objects and advantages are provided by a novel portable evidence preservation system comprising a housing having a generally sealed chamber for storing and transporting forensic evidence therein. Means are provided for providing a supply of air to the chamber, and for maintaining the supply of air at a predetermined temperature and at a predetermined humidity. Filtering means is provided for filtering the supply of air to and/or from the chamber.

The filtering means may be effective to remove at least 99.97 percent of particles down to 0.3 microns. The predetermined temperature may comprise about 35 degrees Fahrenheit to about 45 degrees Fahrenheit, and the predetermined humidity may comprise about 15 percent relative humidity to about 25 percent relative humidity. Means may be provided for recirculating the supply of air through the chamber.

Another embodiment according to the present invention for an evidence preservation system comprises a housing having a first chamber and a second chamber for storing and transporting forensic evidence therein. Means are provided for providing a supply of air to the chamber, and for maintaining the supply of air at a predetermined temperature and at a predetermined humidity. First and second filtering means are provided for separately filtering the supply of air to and/or from the first chamber and the second chamber.

The first and second filtering means may be effective to remove at least 99.97 percent of particles down to 0.3 microns. Third and fourth filtering means may be provided for separately filtering the supply of air from the first chamber and from the second chamber. Means may be provided for recirculating the supply of air through the chamber.

Another embodiment according to the present invention for an evidence preservation system comprises a housing having a plurality of chambers for storing and transporting forensic evidence therein, an HVAC unit for providing a supply of air to the chambers and for maintaining the supply of air at a predetermined temperature and at a predetermined humidity, and a first plurality of HEPA filters for separately filtering the supply of air to each chamber.

The system may further comprise a microprocessor for monitoring the temperature in the chambers, the humidity in the chambers, and/or access to the chambers, and means for recording over time the temperature in the chambers, the humidity in the chambers, and/or access to the chambers. At least one of the chambers may comprise shelving for storing forensic evidence, means for supporting an evidence storage bag, and a releasably sealable decontamination washdown drain.

The unit may be constructed so as to provide a sturdy, tamper proof construction that safeguards the evidence from theft, tampering, and/or loss.

BRIEF DESCRIPTION OF THE DRAWINGS

These and other objects, advantages and features of the present invention will be more readily understood from the following detailed description of certain preferred embodiments of the present invention, when considered in conjunction with the accompanying drawings in which.

DETAILED DESCRIPTION OF THE INVENTION

According to the present invention, novel portable evidence preservation systems are provided for short and long term storage and transport of forensic evidence, particularly items of evidence containing blood, fibers, hair, and semen samples, collected, e.g., by police agencies at crime scenes, medical professionals at hospitals, and/or prosecutors. The systems provide secure storage of such items of evidence in one or more cool, dry, contaminate-free, isolated chambers to reduce the likelihood and rate of deterioration of such items of evidence, reduce contamination of such items of evidence, and reduce biological risks to personnel from such items of evidence.

Figure 1:
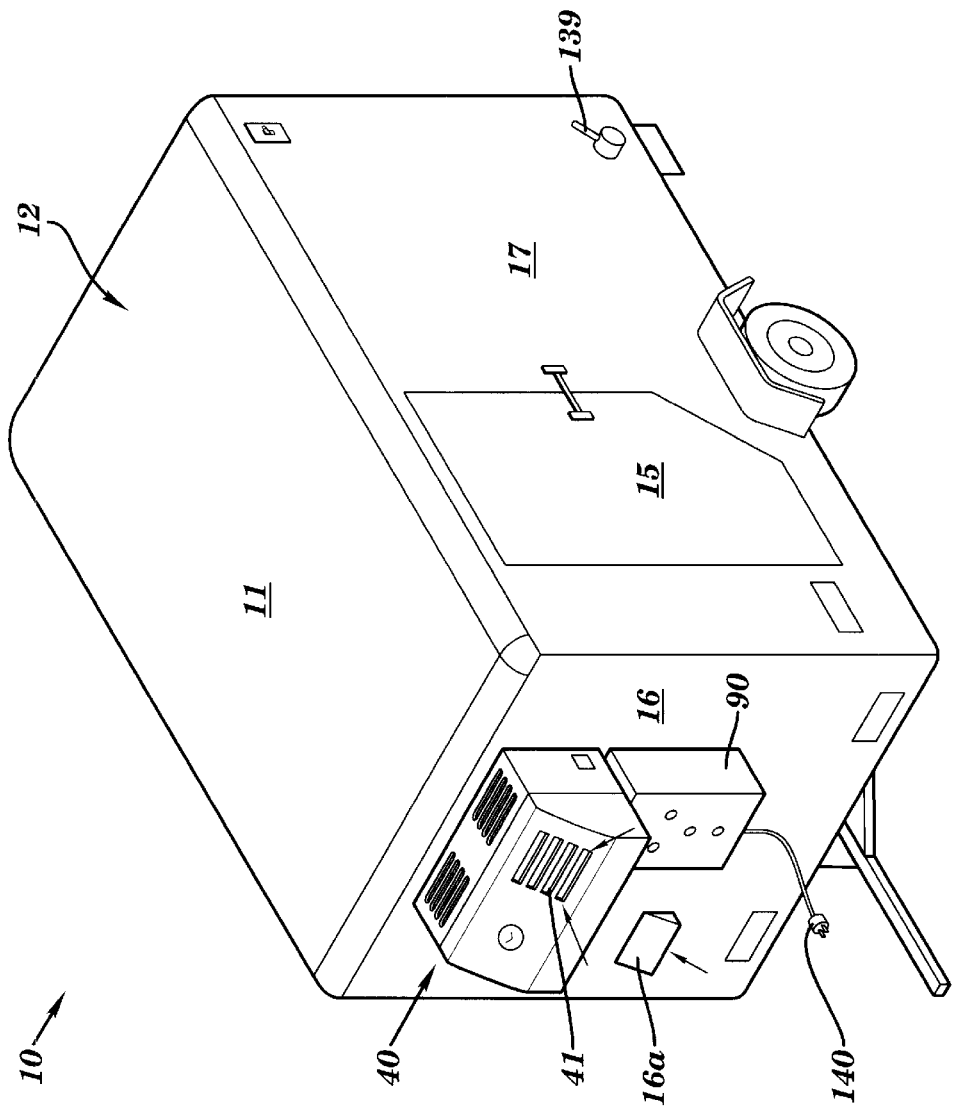
FIG. 1 is a perspective view of one embodiment of a portable evidence preservation system according to the present invention in the form of a trailer.
Figure 2:
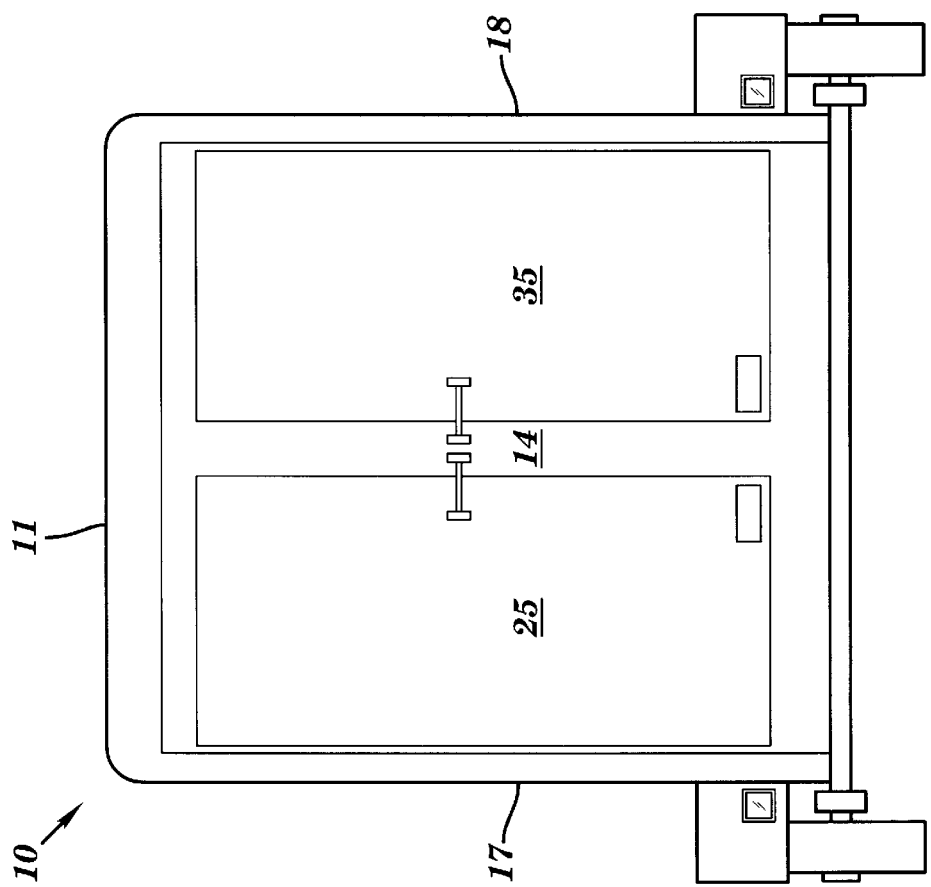
FIG. 2 is an enlarged elevational view of the rear portion of the evidence preservation system shown in FIG. 1.

As shown in FIGS. 1 and 2, one embodiment of a portable evidence preservation system 10 according to the present invention is depicted desirably in the form of a trailer for transporting such items of evidence from a first location to a second location. In this illustrated embodiment, system 10 is readily towed by a vehicle (not shown) between crime scenes, hospitals, police departments, forensic laboratories, and/or court buildings.

Figure 3:
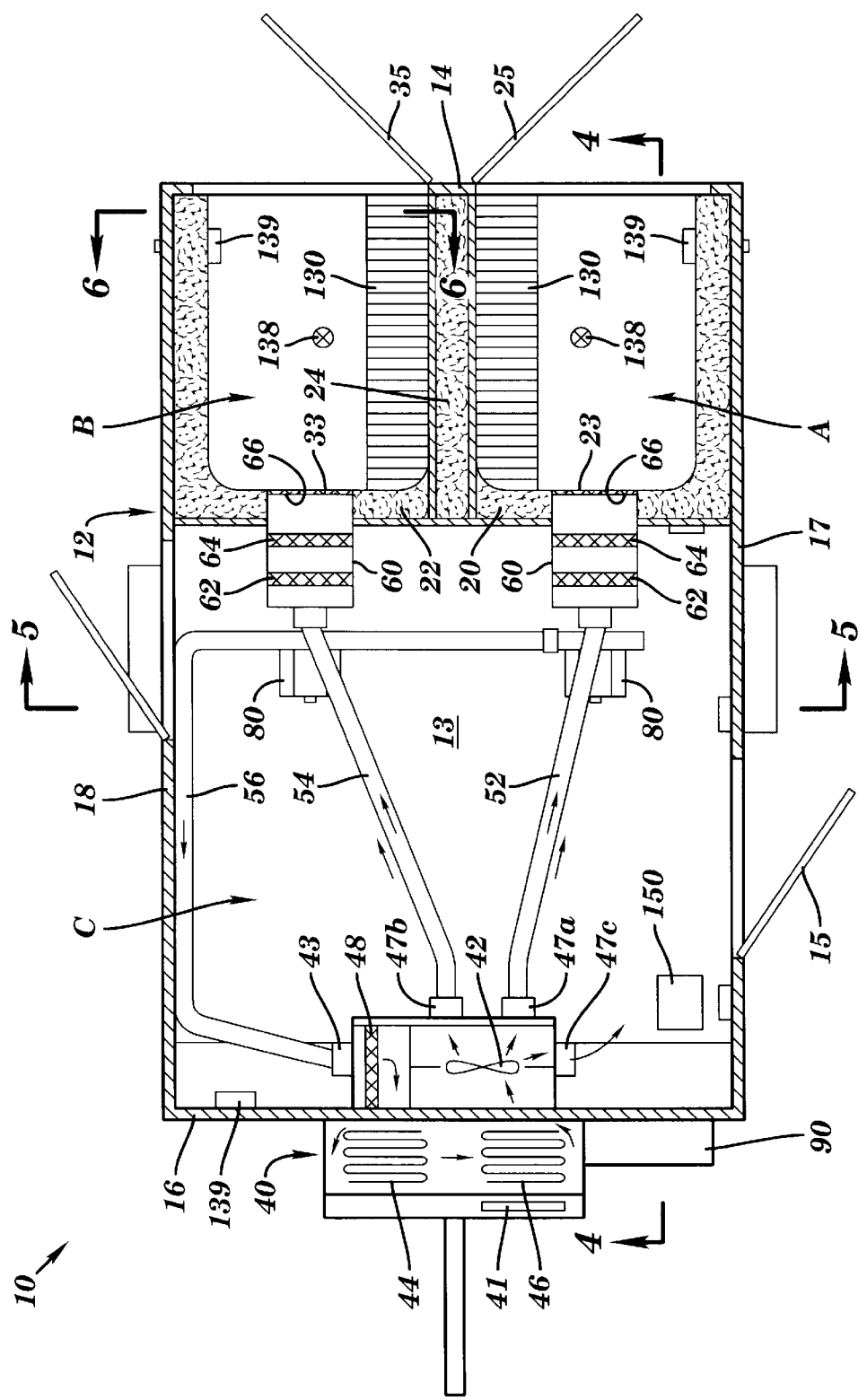
FIG. 3 is a top view of the evidence preservation system shown in FIG. 1 with the top of the trailer removed to illustrate the interior of the system.
Figure 4:
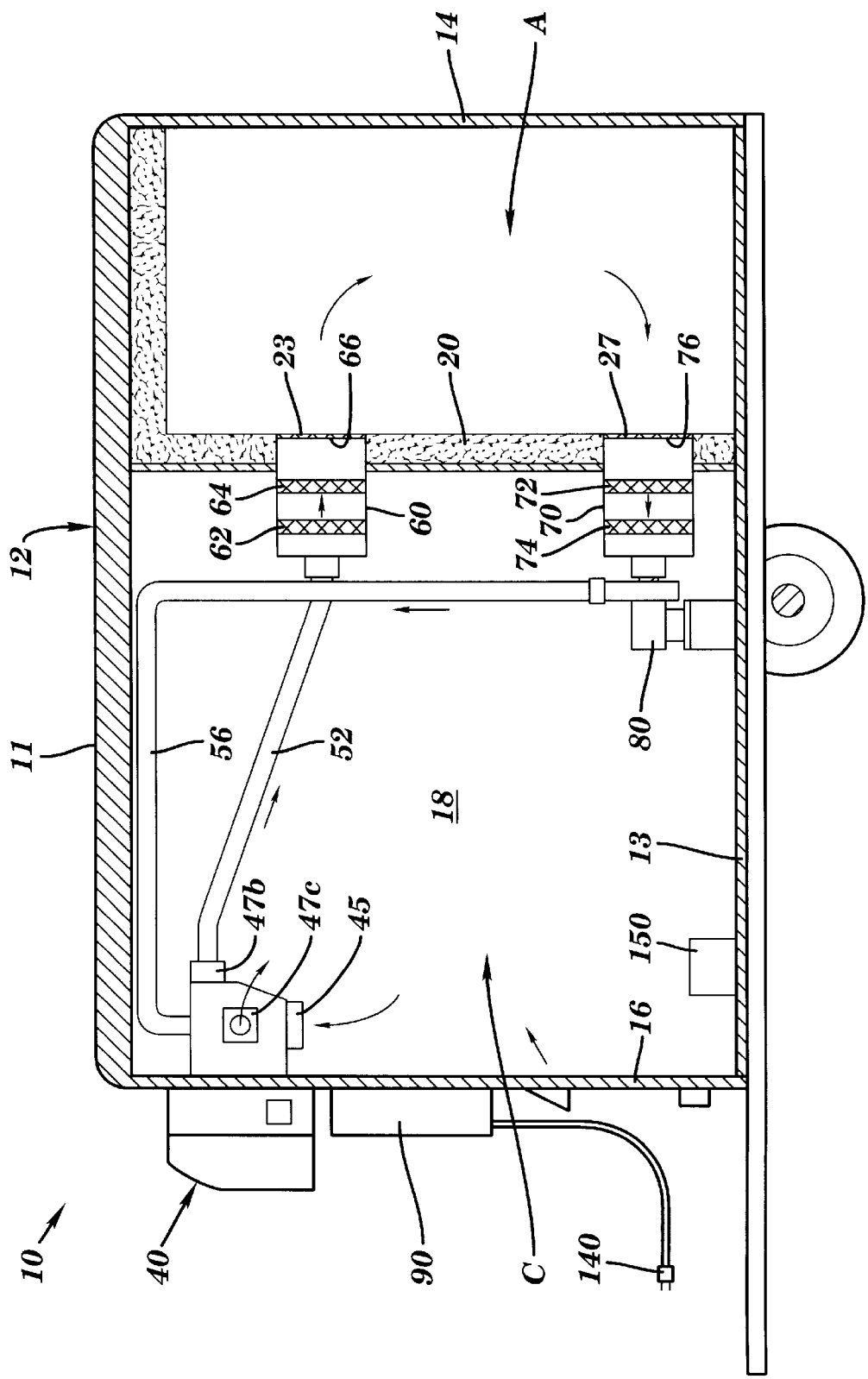
FIG. 4 is a cross-sectional view taken along line 4—4 in FIG. 3.

As shown in FIGS. 3 and 4, exemplary system 10 comprises a housing 12 having a plurality of outer walls and inner walls defining two chambers A and B (FIG. 3) disposed in side-by-side relationship at the rearmost portion of the trailer, and a chamber C disposed at the forward most portion of the trailer. Desirably, collected items of evidence are placed in chambers A, B, and/or C, and system 10 is operated to provide a supply of cool effectively, dry, contaminate-free air to one or more of chambers A, B, and C.

Housing 12 comprises spaced-apart horizontally disposed outer top and bottom walls 11 (FIG. 3) and 13, respectively, a vertically extending outer rear wall 14, a vertically extending outer front wall 16, a pair of vertically extending outer side walls 17 (FIG. 3) and 18, and vertically extending inner walls 20, 22, and 24 (FIG. 3).

In particular, portions of spaced-apart top and bottom walls 11 and 13, a portion of rear wall 14, a portion of side wall 17, and inner walls 20 and 24 at least partially define chamber A. Portions of spaced-apart top and bottom walls 11 and 13, a portion of rear wall 14, a portion of side wall 18, and inner walls 22 and 24 at least partially define chamber B. Portions of spaced-apart top and bottom walls 11 and 13, front wall 16, portions of side walls 17 and 18, and inner walls 20 and 22 at least partially define chamber C. Access to each of chambers A and B is provided by doors 25 and 35 (FIG. 3), respectively, which sealably engage outer rear wall 14 to isolate the interior of chambers A and B from the outside atmosphere. Access to chamber C is provided by a door 15 (FIG. 3) which sealably engages outer side wall 17 to isolate the interior of chambers C from the outside atmosphere.

The various walls may be fabricated as a unitary plastic structure or from stainless steel and suitably attached to each other, e.g., by welding or by mechanical fasteners and rubber gaskets, so that the chambers are isolated from each other as well as from the outside atmosphere. The various walls and doors may comprise one or more layers of insulation to thermally insulate the chambers from each other as well as from the outside atmosphere.

Chambers A and B may comprise inlets 23 and 33 disposed along a top portion of rear walls 20 and 22, respectively, for receiving a supply of conditioned air, e.g., cool, dry, contaminate-free air, as explained in greater detail below. Chambers A and B further comprise outlets 27 (FIG. 4) and 37 (FIG. 6) disposed along a lower portion of rear walls 20 and 22, respectively, for removal of air from chambers A and B.

System 10 may also comprise an HVAC unit 40 positioned along the upper portion of the front of the trailer for providing a supply of air at a predetermined temperature and at a predetermined humidity (moisture content) to chambers A, B and C.

In one embodiment, chamber C can be adapted and used to store and/or transport non-evidence, support materials such as tools, or personnel.

As best shown in FIG. 3, HVAC unit 40 comprises a blower 42, a heating coil 44, a cooling coil 46, and a filter 48. Heating coil 44 and cooling coil 46 may not be used at the same time, e.g., cooling coil 46 is used when air is too warm and heating coil 44 is used when air is too cool. Filter 42 may be a disposable filter consisting of loosely packed fibers coated with an odorless adhesive material for capturing large dust particles from both return and outside air to keep the various components of the HVAC unit clean.

HVAC unit 40 may also comprise a fresh air intake vent 41 (best shown in FIG. 1) for receiving outside air, a first air intake 43 for receiving air from chambers A and B, a second air intake 45 (FIG. 4) for receiving air from chamber C, air discharges 47a, 47b, and 47c for providing a supply of air to chambers A, B, and C, respectively. HVAC unit 40 may further comprise suitable dampers (not shown) for regulating, e.g., obstructing or closing off, the flow of air through air intake vent 41, first air intake 43, second air intake 45, and air discharges 47a, 47b, and 47c.

Figure 5:
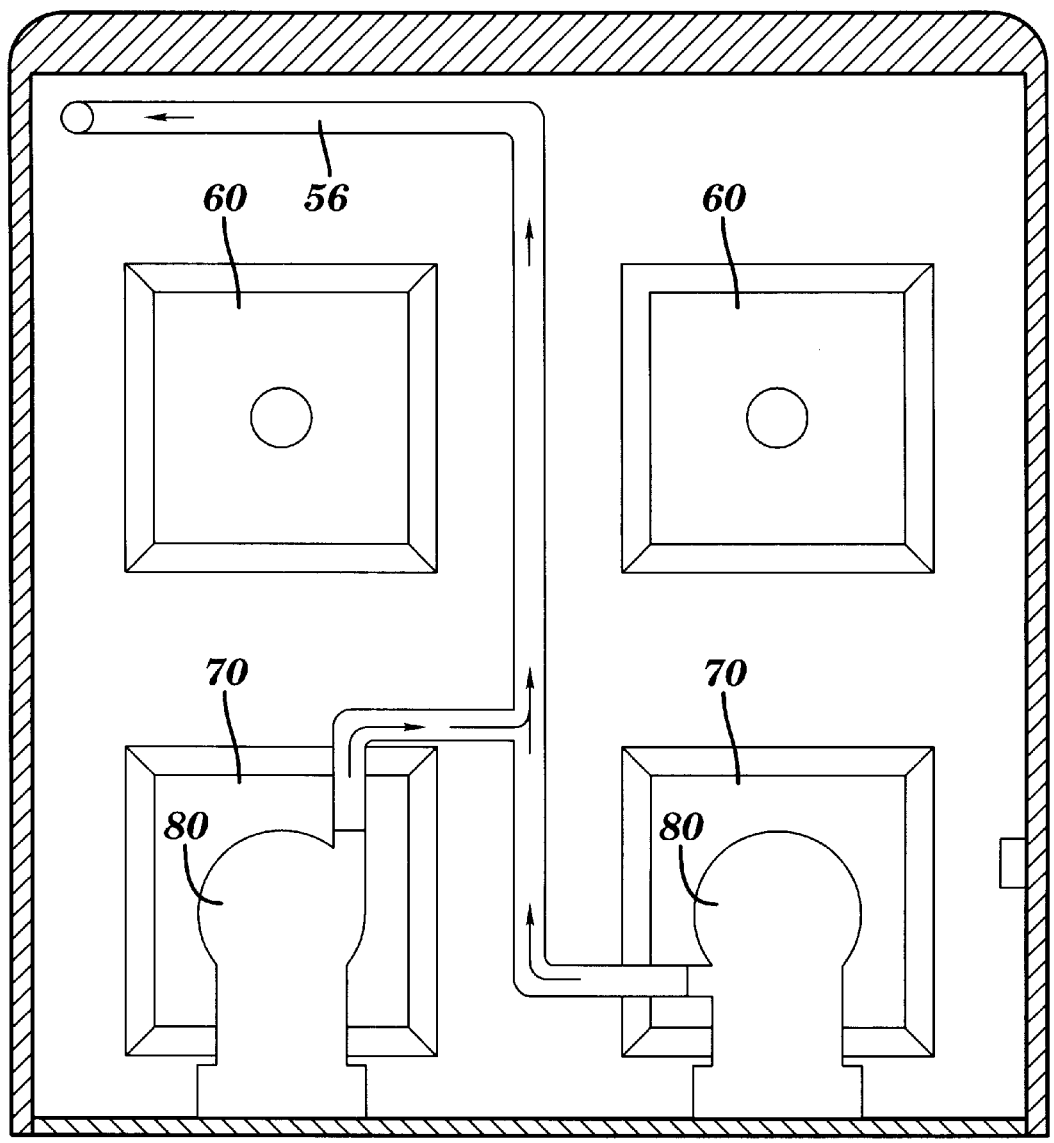
FIG. 5 is a cross-sectional view taken along line 5—5 in FIG. 3.

Air discharges 47a and 47b of HVAC unit 40 are connected to chambers A and B by separate supply ducts 52 and 54, respectively. Supply ducts 52 and 54 attach at one end to air discharge 47a and 47b, and at the opposite end to plenum boxes 60 which, in turn, attach to inlets 23 and 33 of chambers A and B, respectively. Air intake 43 of HVAC unit 40 is connected to chambers A and B by a return conduit 56 which attaches to separate fans 80, each of which attaches to plenum boxes 70 (FIG. 5) which, in turn, attach to the outlets 27 (FIG. 4) and 37 (FIG. 6) of chambers A and B, respectively.

HVAC unit 40 may be operable to provide and circulate a supply of air through system 10 having a temperature of about 35 degrees Fahrenheit to about 45 degrees Fahrenheit, and in one embodiment having a temperature of about 40 degrees Fahrenheit. HVAC unit 40 may also be operable to provide the supply of air having a humidity of about 15 percent relative humidity to about 25 percent relative humidity, and in one embodiment about 20 percent relative humidity. A suitable HVAC unit is available from CARRIER of Syracuse, N.Y.

As shown in FIGS. 3 and 4, each of plenum boxes 60 and 70 may be provided with a plurality of filters for effectively removing particles from the cool dry air supplied to chambers A and B. Each of plenum boxes 60 and 70 may be provided with prefilters 62 and 72, HEPA-type filters 64 and 74, and stainless steel mesh gratings 66 and 76, respectively. Prefilters 62 and 72 may be sealably mounted across the downstream portion of plenum 60 and 70, and HEPA-type filters 64 and 74 may be sealably mounted across the upstream portion of plenum boxes 60 and 70. Stainless steel mesh gratings 66 are mounted across inlets 23 and 33, and stainless steel mesh gratings 76 are mounted across outlets 27 and 37 (FIG. 6) of chambers A and B. Each of the plenum boxes may comprise frames for releasably mounting the prefilter, HEPA filter and stainless steel mesh grating in place and allowing for easy removal for cleaning and/or replacement.

Specifically, HEPA-type filters may remove 99.97% of particles down to 0.3 microns (which includes bacteria, fungal and other opportunistic micro biologicals). HEPA (High Efficiency Particulate Arrestance) filters were developed by the Atomic Energy Commission during World War II to remove and capture radioactive dust particles from the air which might escape and present a health hazard to researchers.

Typically, HEPA filters comprise a deep bed of randomly positioned micro glass fibers. The passages through which the air flow are not straight, but are very tortuous, with many twists and turns. As particles or particulate matter impact on the fibers and adhere to them, the passages become smaller and the filter increase in efficiency.

Prefilters 62 and 72 may be used to protect HEPA filters 64 and 74, and are periodically cleaned or changed to extend the life of HEPA filters 64 and 74. Prefilters can be a fiberglass, polyester, cotton or a blend of these materials which can be pleated for removal of particles larger than 10 microns in size. Due to the high efficiency HEPA filters 64 and 74, fans 80 aid the circulation of air through the chambers.

While it the invention has been described with the use of HEPA-type filters, it will be appreciated to those skilled in the art that filters which are more effective in removing particles from a flow of air than HEPA filters would be suitable. In addition, filters having fibers further apart and which provide lower capture efficiency (i.e., will not capture as many of the small airborne particles as true HEPA filters) are also suitable for use in the disclosed evidence preservation system.

According to the present invention, system 10 reduces deterioration and/or contamination of evidence, particularly, items of evidence containing blood, fibers, hair, and semen samples stored in the chambers. By reducing the humidity and/or the temperature of the air supplied to the chambers, the likelihood or rate of biodegradation of the items of evidence, e.g., biostains (blood and semen), by bacterial digestion of DNA and other proteins is significantly reduced.

In addition, prefilters 62 and 72, and HEPA filters 64 and 74, in particular, reduce contamination of the evidence stored in chambers A, B, and/or C, e.g., among items of evidence in each chamber, items of evidence in different chambers, i.e., cross-contamination, and from the outside atmosphere.

Furthermore, the HEPA filters are also effective in trapping particles, e.g., airborne living organisms such as bacteria. Since dry air kills bacteria, the cool, dry air from HVAC unit 40 is effective to kill the bacteria and/or inhibit the bacteria from breeding within the filter. From the present description, it will be appreciated to those skilled in the art that treating the HEPA filter, e.g., with chemicals, can also kill bacteria in the HEPA filter. In addition, system 10 can include use of germicidal ultra violet light for killing bacteria in the flow of air through the system.

Figure 6:
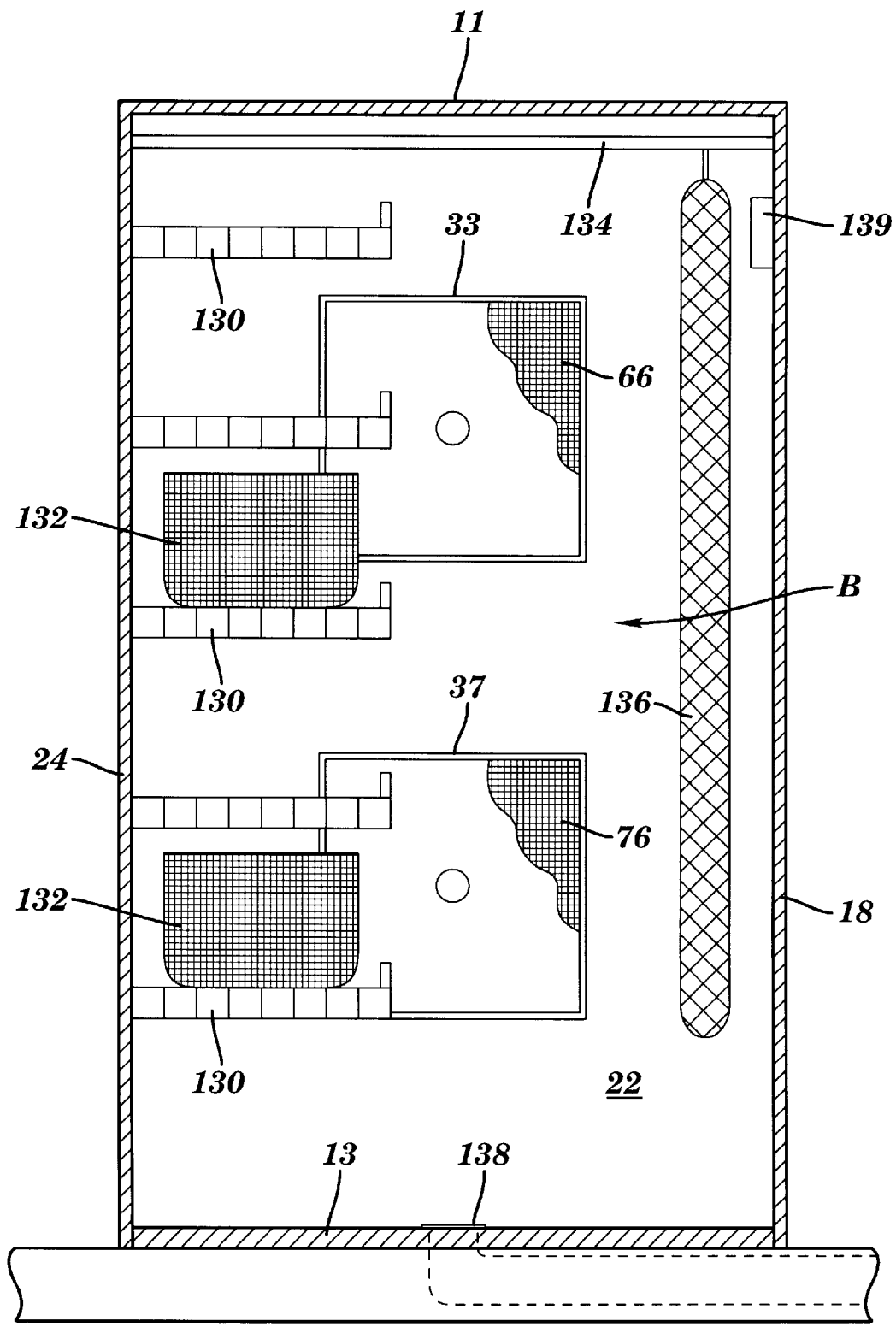
FIG. 6 is an enlarged cross-sectional view taken along line 6—6 in FIG. 3.

As shown in FIGS. 3 and 6, chambers A and B may comprise a plurality of adjustable shelves 130 for supporting a plurality of evidence baskets 132 (FIG. 6) thereon and chambers A and/or B may comprise an elongated member 134 (FIG. 6) which spans between and along the top of side walls 24 and 18 for supporting an evidence storage bag 136 therefrom (FIG. 6). Releasably sealable drains 138 manually operable by handle 139 (FIG. 1) may be provided in each chamber for draining liquid used in cleaning the chambers during a decontamination washdown. Suitably mounted lights 139 illuminate the interior of chambers A, B, and C.

With reference again to FIGS. 1, 3, and 4 the system may comprise an electrical plug 140 which is readily connected to an electrical extension cord which, in turn, is readily connected to an electrical outlet of a building, e.g., a 110 or 220 VAC outlet, for powering the HVAC unit, the fans, and the control panel. It will be appreciated that system 10 can be powered by a battery 150 or a generator (not shown). In addition, the battery or generator can provide a backup supply of power, e.g., when the system is transported between locations.

Figure 7:
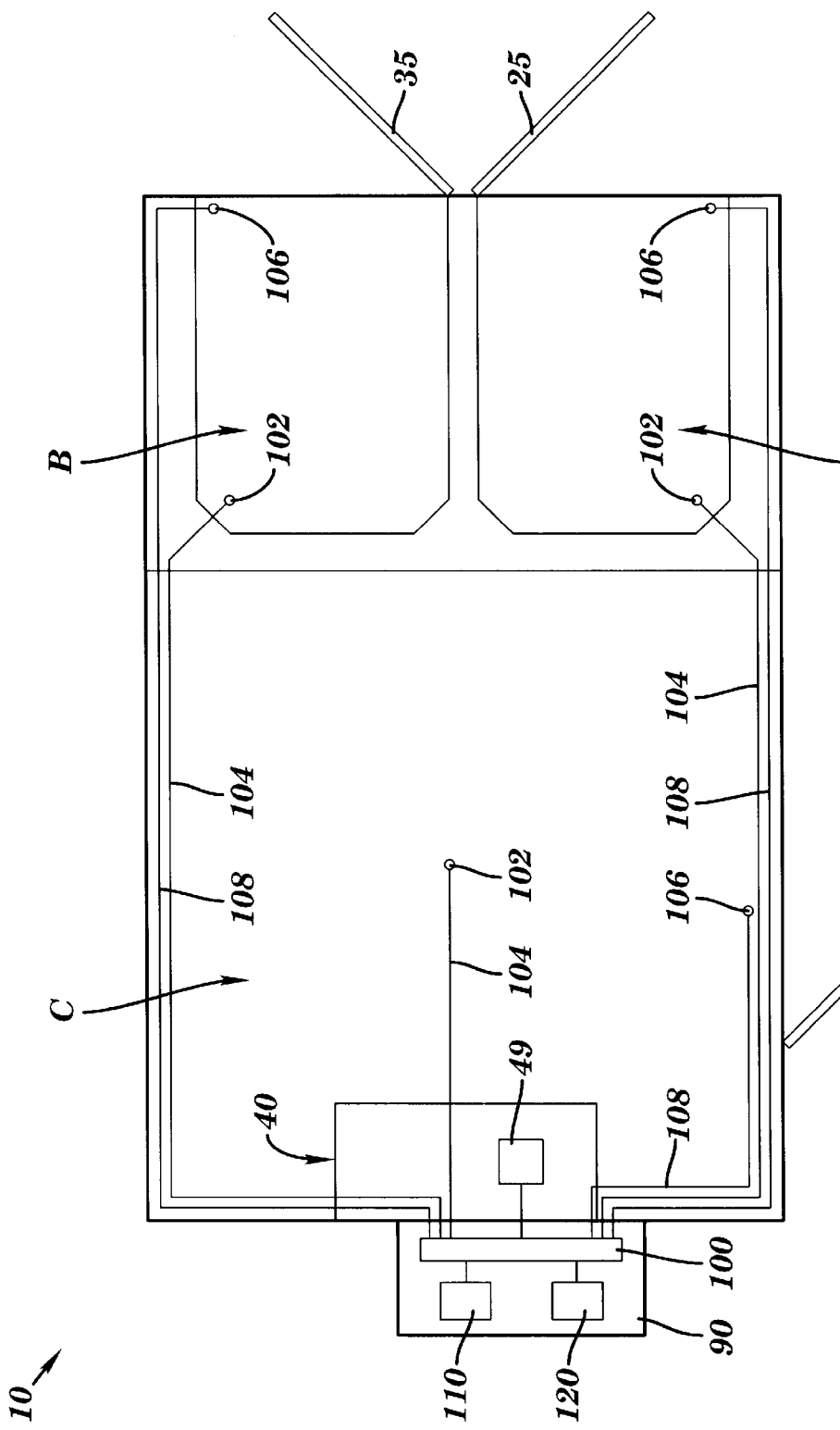
FIG. 7 is a diagrammatic illustration of the control panel and sensors for the system shown in FIG. 1.

In one embodiment of the evidence preservation system, system 10 comprises a control panel 90 for monitoring the temperature and the humidity of the air supplied to the chambers, as well as monitoring access to the chambers. FIG. 7 diagrammatically illustrates system 10 in which control panel 90 desirably comprises a microprocessor 100. Suitable temperature and humidity sensors 102, located in chambers A, B, and/or C, are connected by electrical wires 104 to microprocessor 100. Access to each of chambers A, B, and/or C, is monitored by suitable sensors 106 disposed adjacent doors 15, 25 and 35, respectively. Sensors 106 are connected to microprocessor via wires 108. From the present description, it will be appreciated to those skilled in the art that the sensors can be placed in other locations in the chambers. In addition, microprocessor 100 can be connected to and provide feed back to a control mechanism 49 of HVAC unit 40 for regulating the temperature and humidity of the air supplied to chambers A, B, and/or C.

Control panel 90 may comprise recording means 110 for recording over time the temperature and humidity of the chambers, and for recording access to the chambers. For example, recording means 110 can comprise an electronic memory, a hard drive, a floppy disk drive, or a magnetic tape drive, operably connected to microprocessor 100. In addition, microprocessor 100 can be operably connected to input means 120, e.g., a keyboard, for receiving input from personnel which can also be recorded by recording means 110 to aid in documenting the "chain of custody" of the evidence.

While evidence preservation system 10 is illustrated as configured as a trailer-mounted unit which can be readily transported from a first location to a second location, from the present description it will be appreciated to those skilled in the art that the system can be mounted on a vehicle, e.g., a truck, as well as the system being reduced in size to a lightweight, self-contained unit which is readily carried by a single person for use, particularly when only a small amount of evidence is to be collected, stored, and transported.

It will also be appreciated to those skilled in the art that the evidence preservation system can comprise two separate HVAC units and associated supply and return conduits to further reduce cross-contamination between the chambers. In addition, it will also be appreciated that while HVAC units typically include a filter for filtering large particles, as described above, such a filter may not be necessary since system 10 includes use of more efficient HEPA-type filters.

With reference again to FIGS. 1 and 3, in one mode of operation of system 10, HVAC unit 40 supplies cool, dry air to each of chambers A, B, and C, to reduce degradation of evidence contained therein, particularly from bacteria, and the HEPA filters trap and capture airborne particles in the chambers. During operation, a portion of the supply or air is received from the outside atmosphere through air intake vent 41 as well as an auxiliary vent 16a (FIG. 1), desirably configured as a one way or check valve, should the pressure in the chambers be less than the outside atmosphere. Positioning the HEPA filters upstream from each of chambers A and B, and downstream from each of chambers A and B, isolates chambers A and B from particulate contaminates in each other as well as from chamber C. In addition, the arrangement of HEPA filters isolates chambers from particulate contaminates from both chambers A and B.

In another mode of operation of system 10, the system can be configured, by operating suitable dampers or vents, to supply air solely to chamber A, e.g., by closing or obstructing the flow of air through air discharges 47b and 47c. In addition, by closing first air intake vent 41, second air intake 45, and auxiliary air vent 16a, chamber A can be isolated from the outside atmosphere. In this configuration, air will be recirculated through the system and particularly recirculated through the HEPA filters. In this configuration a greater percentage of particles will be removed over time compared to if the supply of air or a portion thereof is received or replenished from the outside. In addition, recirculation of the air in a closed loop reduces the possibility of airborne bacteria from entering the system from outside the system.

In still another mode of operation of system 10, the system can be configured to supply air to solely chambers A and B, i.e., not supply air to chamber C, e.g., by closing or obstructing the flow of air through air discharge 47c. In addition, by closing air intake vent 41, second air intake 45, and auxiliary vent 16a, chambers A and B can be isolated from the outside atmosphere. In this configuration, since the air is recirculated through the system and particularly recirculated through the HEPA filters positioned upstream from each chamber and downstream from each chamber, items of evidence in one chamber are isolated from contamination from items of evidence in the other chamber. As in the previously described mode, in this configuration a greater percentage of particles will be removed over time compared to if the supply of air or a portion thereof is received or replenished from the outside atmosphere. In addition, recirculation of the air in a closed loop reduces the possibility of airborne bacteria from entering the system from outside the system.

In a further mode of operation of system 10, the system can be configured, by suitably operating the HVAC unit and/or the fans, to supply air to chambers A and/or B at a pressure less than the outside atmosphere, e.g., to provide a negative pressure differential between chambers A and/or B, and the outside, to keep evidence, particulates, odors, and/or airborne pathogens from escaping upon opening and closing the doors.

Thus, while various embodiments of the present invention has been illustrated and described, it will be appreciated to those skilled in the art that many changes and modifications may be made there onto without departing from the spirit and scope of the invention.

What is claimed is:

1. A portable evidence preservation system for storing and transporting forensic evidence, said system comprising:
   means for storing and transporting forensic evidence in a sealable chamber;
   means for providing a supply of air to said chamber;
   means for maintaining the supply of air at a predetermined humidity and at a predetermined temperature; and
   means for filtering the supply of air to said chamber.

2. The system according to claim 1, wherein said means for providing the supply of air comprises supplying air to and from said chamber, and said filtering means comprises filtering the supply of air to and from said chamber.

3. The system according to claim 1, wherein said filtering means is effective to remove at least 99.97 percent of particles down to 0.3 microns.

4. The system according to claim 1, wherein said predetermined temperature comprises about 35 degrees Fahrenheit to about 45 degrees Fahrenheit, and said predetermined humidity comprises about 15 percent relative humidity to about 25 percent relative humidity.

5. The system according to claim 4, wherein said predetermined temperature comprises about 40 degrees Fahrenheit, and said predetermined humidity comprises about 20 percent relative humidity.

6. The system according to claim 1, further comprising means for recirculating the supply of air through said chamber.

7. A portable evidence preservation system for storing and transporting forensic evidence, said system comprising:
   a housing comprising a first chamber and a second chamber for storing and transporting forensic evidence therein, said housing having a first inlet into said first chamber, a first outlet from said first chamber, a first access point for accessing said first chamber, a second inlet into said second chamber, a second outlet from said second chamber, and a second access point for accessing said second chamber;
   means for providing a supply of air to said first chamber and said second chamber;
   means for maintaining the supply of air at a predetermined temperature and at a predetermined humidity; and
   first means and second means for separately filtering the supply of air to said first inlet of said first chamber and to said second inlet of said second chamber.

8. The system according to claim 7, wherein said means for providing the supply of air comprises supplying air to and from said chambers, and said first and second filtering means comprise means for separately filtering the supply of air to and from said chambers.

9. The system according to claim 7, wherein each of said first and second filtering means is effective to remove at least 99.97 percent of particles down to 0.3 microns.

10. The system according to claim 7, wherein said predetermined temperature comprises about 35 degrees Fahrenheit to about 45 degrees Fahrenheit, and said predetermined humidity comprises about 15 percent relative humidity to about 25 percent relative humidity.

11. The system according to claim 10, wherein said predetermined temperature comprises about 40 degrees Fahrenheit, and said predetermined humidity comprises about 20 percent relative humidity.

12. The system according to claim 9, further comprising third means for filtering the supply of air from said first outlet of said first chamber, fourth means for filtering the supply of air from said second outlet of said second chamber, and wherein each of said third and fourth filtering means is effective to remove at least 99.97 percent of particles down to 0.3 microns.

13. The system according to claim 7, further comprising means for recirculating the supply of air through said first and/or second chambers.

14. A portable evidence preservation system for storing and transporting forensic evidence, said system comprising:
   a housing having a plurality of chambers for storing and transporting forensic evidence therein, each of said chambers having an inlet, an outlet, and an access point for accessing said chamber; and
   an HVAC unit for providing a supply of air to said inlets of said chambers and for maintaining the supply of air at a predetermined temperature and at a predetermined humidity; and a first plurality of HEPA-type filters for separately filtering the supply of air to each of said chambers.

15. The system according to claim 14, further comprising means for recirculating the supply of air through said chambers.

16. The system according to claim 14, wherein said predetermined temperature comprises about 35 degrees Fahrenheit to about 45 degrees Fahrenheit, and said predetermined humidity comprises about 15 percent relative humidity to about 25 percent relative humidity.

17. The system according to claim 16, wherein said predetermined temperature comprises about 40 degrees Fahrenheit, and said predetermined humidity comprises about 20 percent relative humidity.

18. The system according to claim 14, further comprising a plurality of fans for aiding the circulation of the supply of air through each of said first plurality of HEPA-type filters.

19. The system according to claim 14, further comprising a first plurality of prefilters for filtering the supply of air to each of said first plurality of HEPA-type filters.

20. The system according to claim 14, further comprising a second plurality of HEPA-type filters for separately filtering said supply of air from said outlets of each of said chambers.

21. The system according to claim 20 further comprising a first plurality of prefilters for filtering the supply of air to each of said first plurality of HEPA-type filters and a second plurality of prefilters for filtering the supply of air to each of said second plurality of HEPA-type filters.

22. The system according to claim 14, further comprising a microprocessor for monitoring at least one of temperature in said chambers, humidity in said chambers, and access to said chambers.

23. The system according to claim 22, further comprising temperature and humidity sensors in said chambers, said temperature and humidity sensors being operably connected to said microprocessor.

24. The system according to claim 23, further comprising access sensors in said chambers, said access sensors being operably connected to said microprocessor.

25. The system according to claim 22, wherein said microprocessor comprises means for recording over time said at least one of temperature in said chambers, humidity in said chambers, and access to said chambers.

26. The system according to claim 14, further comprising a microprocessor for monitoring temperature in said chambers, humidity in said chambers, and access to said chambers, and means for recording over time said temperature in said chambers, humidity in said chambers, and access to said chambers.

27. The system according to claim 14, wherein at least one of said chambers comprise shelving for storing forensic evidence.

28. The system according to claim 27, wherein at least one of said chambers comprises means for supporting an evidence storage bag.

29. The system according to claim 28, wherein said chambers comprise a releasably sealable decontamination washdown drain.

30. The system according to claim 14, further comprising means for receiving power for powering said system.

31. The system according to claim 14, further comprising means for powering said system.

32. The system according to claim 14, wherein said housing comprises a trailer for transporting said system from a first location to a second location.

33. A method for storing and transporting forensic evidence, comprising:

providing a portable evidence preservation system having a chamber as defined in claim 1 at a first location;

obtaining forensic evidence;

placing said forensic evidence in said chamber;

operating said system to store said forensic evidence; and transporting said portable evidence preservation system to a second location.

34. A method for storing and transporting forensic evidence, comprising:

providing a portable evidence preservation system having a plurality of chambers as defined in claim 14 at a first location;

obtaining forensic evidence;

placing said forensic evidence in said plurality of chambers;

operating said system to store said forensic evidence; and transporting said evidence preservation system to a second location.

35. A method for storing and transporting forensic evidence, comprising:

providing a portable evidence preservation system having a first chamber and a second chamber as defined in claim 7 at a first location;

obtaining forensic evidence;

placing said forensic evidence in said first chamber and second chamber;

operating said system to store said forensic evidence; and transporting said portable evidence preservation system to a second location.

36. The method of claim 33, wherein the operating said system comprises maintaining said chamber at a temperature of about 35 degrees Fahrenheit to about 45 degrees Fahrenheit and at a humidity of about 15 percent relative humidity to about 25 percent relative humidity.

37. The method of claim 33, further comprising operating the system to maintain the chamber at a subatmospheric pressure.

38. The method of claim 34, wherein the operating said system comprises maintaining said chamber at a temperature of about 35 degrees Fahrenheit to about 45 degrees Fahrenheit and at a humidity of about 15 percent relative humidity to about 25 percent relative humidity.

39. The method of claim 34, further comprising operating the system to maintain the plurality of chambers at a subatmospheric pressure.

40. The method of claim 35, wherein the operating said system comprises maintaining said chamber at a temperature of about 35 degrees Fahrenheit to about 45 degrees Fahrenheit and at a humidity of about 15 percent relative humidity to about 25 percent relative humidity.

41. The method of claim 35, further comprising operating the system to maintain the first chamber and the second chamber at a subatmospheric pressure.

42. The system according to claim 1, further comprising forensic evidence.

43. The system according to claim 7, further comprising forensic evidence.

44. The system according to claim 14, further comprising forensic evidence.

45. The system according to claim 1, wherein said chamber comprises a releasably sealable decontamination washdown drain.

* * * * *